United States Patent [19]

Vandersteen

[11] Patent Number: 5,202,533
[45] Date of Patent: Apr. 13, 1993

[54] DRUG INJECTION APPARATUS FOR AN ANIMAL

[76] Inventor: Douglas G. A. Vandersteen, Box 98, Chatfield, Manitoba, Canada, R0C 0N0

[21] Appl. No.: 826,360

[22] Filed: Jan. 28, 1992

[51] Int. Cl.$^5$ .................. F42B 12/54; A61M 5/20
[52] U.S. Cl. ...................... 102/512; 102/371; 102/504; 273/418; 604/135; 604/208; 604/218; 604/219
[58] Field of Search ............... 604/130, 131, 134, 135, 604/187, 207, 208, 219, 221, 222, 218; 273/418; 102/502, 504, 512, 371; 42/1.14

[56] References Cited

U.S. PATENT DOCUMENTS

| | | | |
|---|---|---|---|
| 1,561,854 | 11/1925 | Hein | 604/219 |
| 2,348,337 | 5/1944 | Francis | 102/512 |
| 2,854,925 | 10/1958 | Crockford et al. | |
| 3,207,157 | 9/1965 | Murdoch | 604/130 |
| 3,314,286 | 4/1967 | Hickerson et al. | 102/504 |
| 3,334,788 | 8/1967 | Hamilton | 604/135 |
| 3,747,247 | 7/1973 | McNau | 42/1.14 |
| 4,106,770 | 8/1978 | Gray | 273/418 |
| 4,312,347 | 1/1982 | Magoon et al. | 604/135 |
| 4,799,906 | 1/1989 | Perkins, Jr. | 102/504 |
| 4,822,340 | 4/1989 | Kamstra | 604/135 |
| 4,863,428 | 9/1989 | Chevalier | 102/512 |

*Primary Examiner*—Harold J. Tudor
*Attorney, Agent, or Firm*—Adrian D. Battison; Stanley G. Ade; Murray E. Thrift

[57] ABSTRACT

A remote injection device for animals comprises a barrel with a piston slideable within the barrel from an initial retracted position at one end of the barrel forwardly toward the opposed end of the barrel to discharge liquid in an injection action through a needle at the forward end of the barrel. The piston is held in a retracted position by an O-ring on a release member which projects through an O-ring carried on the inside surface of the barrel. The inner diameter of the O-ring on the barrel can be adjusted by axial movement of the pair collars on the inside of the barrel. This adjusts the amount of force necessary to push the release member O-ring through the outer O-ring to release the piston to be moved by spring to the discharge position. The barrel can be mounted either upon an arrow type projectile so the impact forces are sufficient to release the piston upon engaging the animal. Alternatively the barrel can be mounted upon a pole with the pole acting to release the piston when pushed forwardly with the needle and barrel in engagement with the animal.

13 Claims, 3 Drawing Sheets

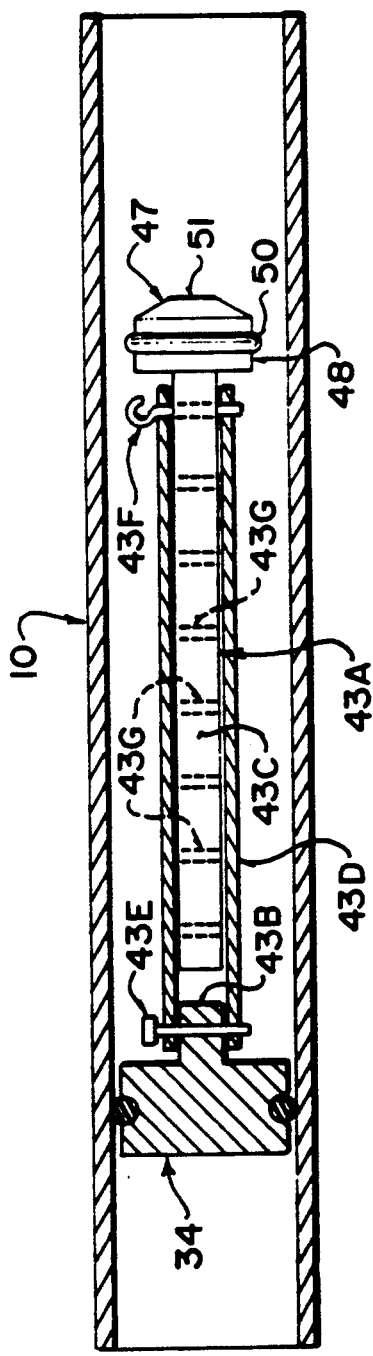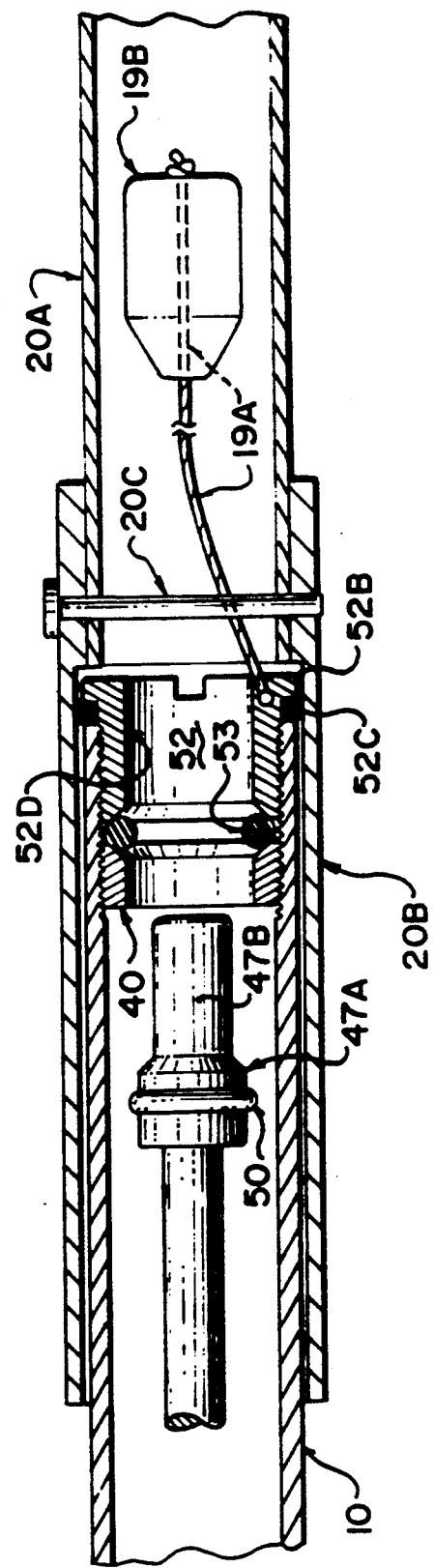
FIG. 4
FIG. 5

DRUG INJECTION APPARATUS FOR AN ANIMAL

This invention relates to a drug injection apparatus for remotely injecting an animal with a liquid.

Many animals even those of a domesticated nature such as cattle, if allowed free range, become wary of human contact and are therefore difficult to catch for medical treatment or other purposes.

In some cases it is merely intended to inject the animal with a dose of medication or other liquid so that it is not worthwhile trapping and holding the animal during this time with of course the risk of injury to the farmer or to the animal.

Remote drug injection systems are therefore available generally comprising a projectile which is simply fired at the animal from a distance with the projectile carrying the medication liquid within a barrel of the projectile and including a system for injecting the liquid material into the animal after the projectile has reached the animal and impacted into the flesh of the animal. It is of course necessary that the injection of the liquid take place only after the impact has occurred to prevent the loss of the liquid during the flight time from the farmer to the animal.

One example of a projectile of this type is shown in U.S. Pat. No. 2,854,925 (Crockford and assigned to Palmer Chemical and Equipment Company). This patent shows a projectile which is intended to be fired by an air rifle with a flighting at the rear end to assist in maintaining the projectile in the required orientation with its axis longitudinal of the flight path. In this embodiment the propulsion of the projectile at the same time actuates a needle which is forced forwardly within the projectile to penetrate a capsule to release a chemical material into a second chemical material which generates gas to force a piston forwardly within a barrel of the projectile to expel the liquid contained within the barrel through an injection needle at the forward end of the barrel. The delay necessary between the firing of the projectile and the injection into the animal is obtained by the chemical reaction.

This system has in practice been superseded by the manufacturer to an arrangement in which an explosive charge is provided at the base of the barrel for forcing the piston forwardly after impact. The explosive charge includes a detonator system which is actuated upon the impact to cause sufficient expansion of gases within the barrel to force the piston forwardly and inject the material.

However the prior art device is unsatisfactory for many reasons. Firstly, it is relatively expensive in that for each actuation of the device it is necessary to provide a separate charge which is of significant cost. Secondly, the device once fired generally remains within the animal until expelled by the animal brushing it off or by the normal action of the flesh of the animal which tends to gradually reject the needle.

Thirdly, the loading of the device with the liquid and with the separate charge is relatively difficult and time consuming particularly out in the field where many of these injections may need to be carried out at a single time.

SUMMARY OF THE INVENTION

It is one object of the present invention, therefore, to provide an improved drug injection apparatus for remotely injecting an animal with a liquid.

According to the invention, therefore, there is provided a drug injection apparatus for remotely injecting an animal with a liquid comprising a cylindrical barrel defining a longitudinal axis of the barrel, a needle assembly at a forward end of the barrel, a piston slideable longitudinally within the barrel from a retracted position remote from the needle assembly, in which a liquid to be injected can be introduced into the barrel between the needle assembly and the piston, and a forward dispensing position in which the piston is moved forwardly to force the liquid through the needle assembly for injecting into the animal, spring means biasing the piston into the forward dispensing position, and a release means actuable to hold the piston in the retracted position and to release the piston to move to the forward dispensing position in response to a forward axial force on the release means, the release means comprising an annular retaining ring member attached to said barrel and held against movement longitudinally thereof and defining a surface facing radially inwardly of the axis of the barrel and a release member connected to the piston so as to be movable longitudinally therewith, the release member being shaped to pass through said retaining ring member and having outwardly facing surface means thereon for engaging said surface of said retaining ring member, at least one of said surface means and said retaining ring member being formed of a resilient material such that said at least one can be deformed to allow passage of said release member through said retaining ring member when an axial force thereon exceeds a predetermined maximum force.

According to the second aspect of the invention there is provided a drug injection projectile for remotely injecting an animal with a liquid comprising a cylindrical barrel defining a longitudinally axis of the barrel, projecting means mounted on the barrel at a rearward end thereof for projecting the barrel in a forward axial direction, a needle assembly a forward end of the barrel, a piston slideable longitudinally within the barrel from a retracted position remote from the needle assembly, in which a liquid to be injected can be introduced into the barrel between the needle assembly and the piston, and a forward dispensing position in which the piston is moved forwardly to force the liquid through the needle assembly for injecting into the animal, spring means biasing the piston into the forward dispensing position, and a release means actuable to hold the piston in the retracted position and to release the piston to move to the forward dispensing position in response to a forward axial force on the release means, the release means comprising an annular retaining ring member attached to said barrel and held against movement longitudinally thereof and defining a surface facing radially inwardly of the axis of the barrel and a release member connected to the piston so as to be movable longitudinally therewith, the release member being shaped to pass through said retaining ring member and having outwardly facing surface means thereon for engaging said surface of said retaining ring member, at least one of said surface means and said retaining ring member being formed of a resilient material such that said at least one can be deformed to allow passage of said release member through said retaining ring member when an axial force thereon exceeds a predetermined maximum force, said predetermined maximum force being arranged such that the momentum of the piston and release member on impact of the barrel with the animal causes sufficient force to allow said release member to be released from the annular retaining ring member for injection of said liquid, said needle assembly including a needle having a retaining member thereon for engaging flesh of the animal to hold the needle in place in the animal during said injection.

According to a third aspect of the invention there is provided a projectile wherein the barrel includes a filling opening at said needle assembly, a portion of the needle assembly being removable to allow access to an interior of the barrel for refilling the barrel between the needle assembly and the piston and for returning the piston to the retracted position.

Embodiments of the invention will be described in conjunction with the accompanying drawings.

DESCRIPTION OF THE DRAWINGS

FIG. 4 is a cross-sectional view similar to that of FIG. 3, showing a modified connecting shaft for the piston allowing simple adjustment of a dose to be dispensed.

FIG. 5 is a further cross-sectional view similar to that of FIG. 3 showing a modified arrangement for attachment to a pole.

In the drawings like characters of reference indicated corresponding parts in the different figures.

DETAILED DESCRIPTION

Figure 1:
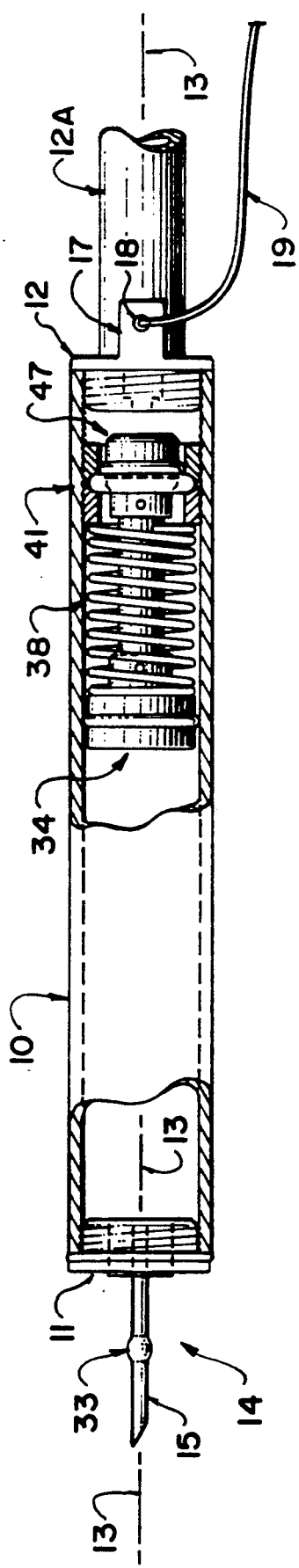
FIG. 1 is a side elevational view partly broken away of an injection apparatus according to the present invention.
Figure 2:
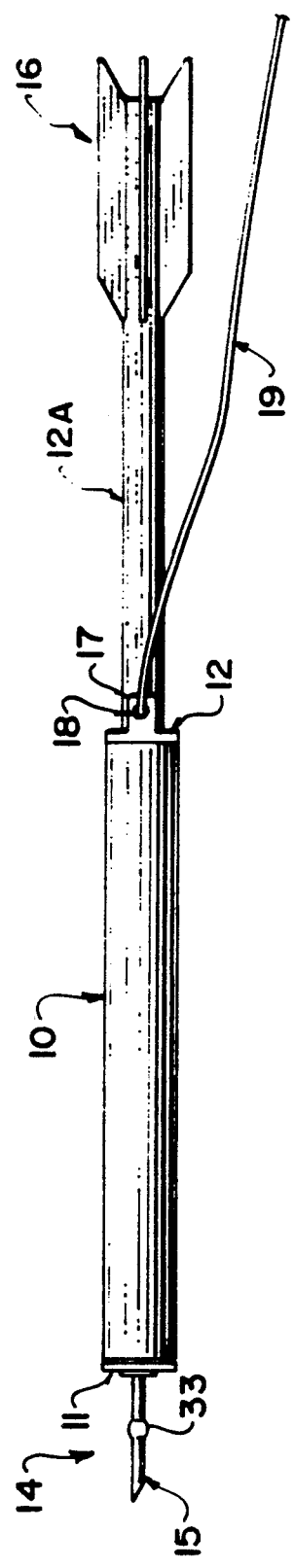
FIG. 2 is a side elevational view of the complete apparatus of FIG. 1.

The injection apparatus comprises a cylindrical barrel 10 with a first end cap 11 at a forward end and a second end cap 12 at a rearward end. The barrel is longitudinal so as to define a longitudinal axis 13. The end cap 11 forms part of a needle assembly generally indicated at 14 including a needle 15 for penetration into the flesh of the animal to be injected. The end cap 12 attaches to a propulsion or handling system for the syringe generally in the form of a rod extending rearwardly from the end cap 12 longitudinal of the axis 13. An embodiment shown in FIG. 2, the end cap 12 is attached to an arrow shaft 15 with a flighting generally indicated at 16 for propulsion by a bow generally of the cross bow type (not shown). The end cap 12 includes a flange portion 17 which includes an opening 18 attached to a tether string 19 the other end of which is attached to a suitable supply (not shown) at the location of the farmer thus allowing the projectile to be maintained tethered to be pulled back to the farmer after the injection is complete or in the event that the animal is missed.

Figure 3:
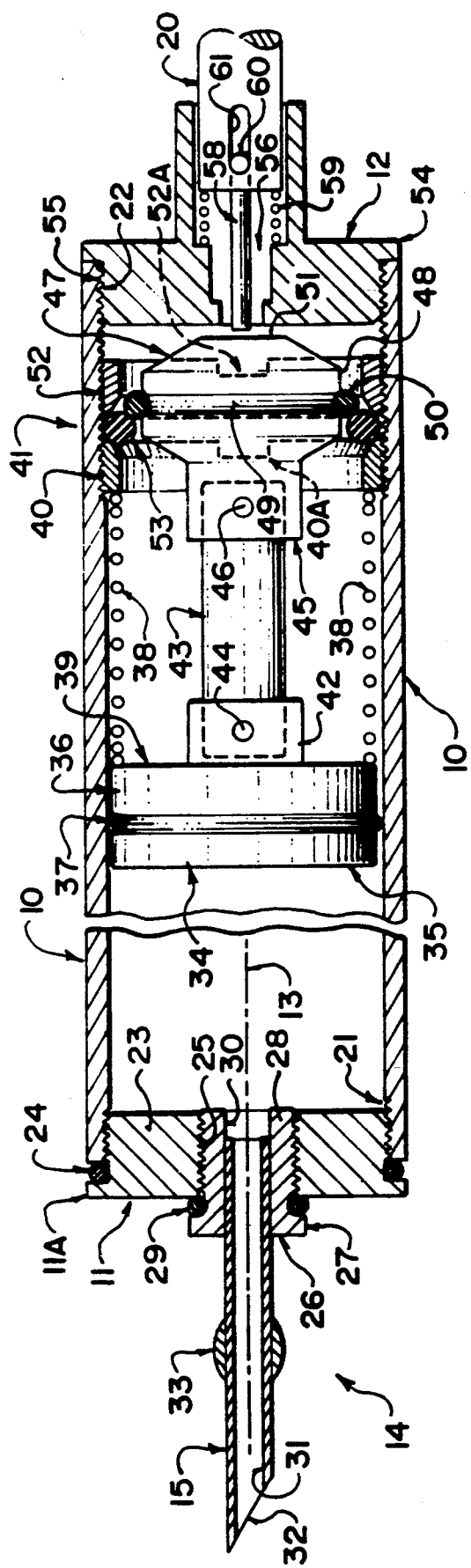
FIG. 3 is a cross sectional view of the apparatus shown in FIG. 1 but separated from the arrow shaft propulsion system and instead attached to a manually operable pole.

In the embodiment shown in FIG. 3, the end cap 12 is attached to a rod or pole 20 which projects outwardly longitudinally along the axis 13 so that the pole can be handled manually. Some animals can be approached to within a few feet but then become wary and maintain a distance of a few feet from the farmer. Such animals can be injected by manipulating the injection device on the end of the pole so that the needle is brought up into contact with the animal by manipulating the pole and then the liquid from the interior of the barrel injected in the manner described hereinafter. Referring therefore particularly to FIG. 3, in both embodiments the barrel comprises a sleeve of circular cross section with a portion thereof at each end which is internally screw threaded as indicated at 21 and 22 respectively. The threaded portion 22 is longer than the threaded portion 21 so as to extend beyond the end cap 12 along the part of the interior of the barrel. The end cap 11 comprises an end flange 11A projecting outwardly beyond the inner face of the barrel together with a cylindrical insert portion 23 which has an external screw thread for cooperating with the internal screw thread 21 on the barrel. An O-ring 24 is located within a groove just behind the flange portion 11A so as the screw threaded cylindrical portion 23 is threaded into the barrel, the O-ring 24 is compressed between the end of the barrel and the flange portion 11A.

The end cap 11 further includes a cylindrical central opening 25 extending along the axis 13. This opening 25 is internally threaded to cooperate with a cap member 26 of the needle assembly. The needle cap member is similarly shaped to the cap member 11 including a flange portion 27 an insert portion 28, the latter being cylindrical and having an external screw thread cooperating within the internal screw thread of the opening 25. The needle cap member can therefore be threaded into place until an O-ring 29 is pressed against the outside face of the cap member 11 by the flange portion 27 of the needle cap member. The needle 15 is carried in a longitudinal bore 30 of the needle cap member so as to project axially outwardly from the end of the needle cap member. The needle is hollow as indicated at 31 and has a chamfered end surface 32 in conventional manner. The needle carries a ferrule 33 at a position along its length which acts to hold the needle in the flesh of the animal during the injection process. The ferrule is simply a metal body provided at a point along the length of the needle which can simply be generally spherical in shape or can be conical to allow an easier insertion than withdrawal. The needle cap member and the needle itself can simply be removed from the cap member 11 by manual grasping of the needle and rotation of the needle and needle cap member to unscrew the threaded coupling to allow access to the interior of the barrel. The barrel is otherwise closed apart from the other end cap member 12.

Inside the barrel is provided a piston 34 generally slideable longitudinally of the barrel to expel a liquid medication contained between a head 35 of the piston and the end cap member 11. This area can be filled during the time that the needle assembly is removed. The piston has a cylindrical outer surface 36 carrying an O-ring 37 to provide a seal. The piston is removable from a retracted position shown in FIG. 3 to a dispensing position in which it is moved forwardly along the axis 13 to a position abutting or in close relationship to the underside of the end cap 11. The piston is biased into the discharged position by a spring 38 which has one end abutting an end face 39 of the piston and a second end abutting a collar 40 provided on the inside of the barrel.

The piston cooperates with a latching and release mechanism generally indicated at 41. The piston has a collar 42 projecting rearwardly from the end face 39 which receives a shaft 43 coupled within the collar by a pin 44. The other end of the shaft 43 is attached to a similar collar 45 by a pin 46 with that collar being attached to a release member 47 forming part of the latch and release mechanism 41. The release member 47 includes a generally cylindrical surface 48 having a groove 49 thereon receiving an O-ring 50 surrounding the cylindrical surface 48 and sitting in the groove. The O-ring is formed from a resiliant material. The release member 47 further includes an end surface 51 which lies in a radial plane of the axis 13. The O-ring 50 also lies in a radial plane of the axis. The collar 40 forms one of a pair of collars 40 and 52 each of which is annular in shape and each of which has an external screw thread cooperating with the threaded portion 22 of the barrel. Each of the collars 40 and 52 can be reinserted into place within the barrel by rotating the collar using a tool engaging a recess 40A and 52A of the collars 40 and 52 respectively. The collar 40 is generally moved to a position at the base of the screw thread 22 at which it provides the abutment surface for the spaced end of the spring 38.

Between the collars of 40 and 52 is provided a second O-ring 53 received within the depression defined between the two collars with an outside surface of the O-ring in contact with the inside surface of the barrel. Each of the collars is chamfered on the side facing the O-ring 53. In an initial relaxed condition of the O-ring 53, the O-ring 53 is simply abutted on each side by the chamfered surface of the respective collars. However, the O-ring 53 can be compressed axially and thus squeezed radially inwardly by rotation of the collar 52 to move the collar 52 toward the collar 40. This axial movement [causes an] of the collar 52 acts as means for adjustment of the inside surface of the O-ring 53 to move that inside surface radially inwardly and outwardly as required. The inside surface of the O-ring 53 thus forms an annual retaining ring facing inwardly for engagement with the O-ring [54] 50.

The outside surface 48 of the release member 47 has a diameter less than of the inside surface of the O-ring 53. However, the O-ring 50 projects outwardly beyond the outside surface 48 to a diameter greater than the inside diameter of the O-ring 53. Thus the release member 47 can slide readily through the O-ring 53 whereas the O-ring 50 abuts against the O-ring 53 and is prevented from sliding or passing therethrough without the application of an axial force to the release member beyond the predetermined maximum, the maximum being adjustable by the axial movement of the collar 52 as explained above.

The end cap 12 comprises a flange portion 54 and a cylindrical insert portion 55 which is threadably engaged with the end of the barrel. The end cap 12 has an axial opening 56.

In operation, the needle assembly including the needle and cap and the needle itself are removed manually by unthreading to expose the interior of the barrel. The piston is then depressed using an elongate tool shaped to project through the opening in the end cap member 11 to press the piston and the release member axially backwardly until the O-ring 50 passes through the O-ring 53 to hold the release member in the retracted position with the spring compressed. The interior of the barrel is then filled with the liquid to be injected. The needle assembly is then replaced closing the barrel. In the embodiment using the arrow type projectile, the arrow is then fired using the conventional cross bow (not shown) and impacts upon the animal so the needle penetrates the animal's flesh down to the end cap with the barrel being impacted against the flesh of the animal. The momentum of the piston and the release member is sufficient to generate a force greater than the predetermined maximum set by the adjustment of the O-ring 53 allowing the O-ring 50 to pass through to the release position so the spring causes the piston to move to dispense the liquid through the needle into the animal. This injection does not take place until the impact has caused the piston to be released. The amount of force necessary to cause this release can be adjusted simply depending upon various factors such as the temperature, the force used to fire the projectile, the viscosity of the liquid. Once the injection has taken place, the string tether 19 can be pulled to extract the projectile from the animal so that it can be retrieved and reused by repeating the above actions. There is therefore no necessity for the farmer to carry any other equipment than the projectile itself and the liquid to be injected which can simply be poured into place from a suitable supply container.

When it is required instead to use the device on the manipulating type pole, the same process is repeated but in this case the end cap 12 is attached to the pole 20. Pole 20 carries a probe 58 which passed through the opening 56 in the end cap to engage the end face 51 of the release member. The pole 20 is spring biased to a position away from the end cap 12 by a spring 59. It is held in place by a pin 60 which moves within a slot 61 provided in the projecting collar of the end cap. Thus normally the injection device is pushed forwardly away from the pole by the spring 59. However when the needle engages the animal, the pole is pushed thus depressing the pole against the action of the spring 59 and causing the probe 58 to pass into the interior of the barrel against the end face of the release member pushing member with a force greater than the predetermined maximum force to release the piston to move to the discharge position.

Turning now to FIG. 4 there is shown a modified arrangement of the connecting shaft indicated in FIG. 4 at 43A which connects between the piston 34 and the release member 47. In this embodiment the shaft 43A is formed in two parts 43B and 43C interconnected by a sleeve 43D. The sleeve is connected at one end by a pin 43E to the portion 43B integral with the piston 34. The sleeve 43D can be connected to the portion 43C at different positions by a pin 43F which extends through a hole in the sleeve 43D and through a selected one of a plurality of holes 43G in the portion 43C. In this way the length of the shaft 43A can be adjusted thus locating the piston 34 at different positions within the cylinder thus varying the dose of medication to be dispensed by varying the distance from the piston to the end cap 11.

This arrangement avoids the necessity for different sizes of cylinder for different doses of medication required. The single equipment therefore carried by the user can be adjusted without the necessity for transporting separate parts and the selecting parts from a kit.

Turning now to FIG. 5, a modified arrangement is shown for mounting upon a pole 20A. In this case the pole is hollow and carries at its end a sleeve 20B attached to the end of a pole by a transverse pin 20C. The sleeve extends along the outside of the cylinder 10 so as to receive the cylinder within the sleeve.

In this embodiment the collar 52A is extended from its engagement with the O-ring 53 to the end of the cylinder 10 at which it forms an outwardly projecting flange 52B which traps an O-ring 52C between the flange 52B and the end of the cylinder 10. The O-ring 52C thus projects outwardly from the outside surface of the cylinder to act as a friction fit on the inside of the sleeve 20B.

In its embodiment, the release member 47A includes an outwardly projecting portion 47B to extend through an opening 52D in the collar 52A. A tether cord 19A is attached to the collar 52A and extends therefrom to weight 19B carried within the pole 20A.

In operation, the syringe cylinder as previously described and the release member forced rearwardly into engagement with the O-ring 53. In this position the projecting portion 47B of the release members extends beyond the collar 52A at the outer end of the cylinder and is therefore available for engagement. The cylinder 10 is then loaded into the sleeve 20B to a position in which the projecting portion 47B just engages the transverse pin 20C. The tether cord 19A is loose within the pole and the weight 19B is retained at some suitable position within the pole. The pole is then brought up and the needle engaged with the animal so that pressure against the animal forces the syringe rearwardly against the pin 20C thus pushing the release member forwardly and causing injection of the medication. If the animal pulls away from the pole due the aggravation of the injection, the syringe is pulled outwardly from the sleeve and thus remains attached to the animal while the injection of the medication continues. The syringe however remains tethered by the string 19A until the weight 19B engages the pin 20C to pull the syringe from the animal at a time after the injection of the medication is complete.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. A drug injection apparatus for remotely injecting an animal with a liquid comprising a cylindrical barrel defining a longitudinal axis of the barrel, a needle assembly at a forward end of the barrel, a piston slidable longitudinally within the barrel from a retracted position remote from the needle assembly, in which a liquid to be injected is introduced into the barrel between the needle assembly and a forward end of the piston, and a forward dispensing position in which the forward end of the piston is moved forwardly to force the liquid through the needle assembly for injecting into the animal, spring means biasing the piston into the forward dispensing position, and a release means actuable to hold the piston in the retracted position and to release the piston to move to the forward dispensing position in response to a forward axial force on the release means, the release means comprising cooperating means having a first portion attached to said barrel and held against movement longitudinally thereof and defining a surface facing radially inwardly of the axis of the barrel and a second portion connected to the piston so as to be movable longitudinally therewith, said cooperating means being shaped for said second portion to pass through said first portion, said cooperating means including an annular O-ring which is formed of a resilient material such that said O-ring can be deformed to allow passage of said second portion through said first portion when an axial force thereon exceeds a predetermined maximum force, and means adjusting said annular O-ring in a radial direction so as to vary said predetermined force.

2. The apparatus according to claim 1 wherein the first and second portions of the cooperating means are both of circular shape in end elevational view so as to cause engagement therebetween around, the full periphery thereof.

3. The apparatus according to claim 1 wherein said means for adjusting said annular O-ring comprises means for longitudinally compressing said annular O-ring to cause said radial adjustment.

4. The apparatus according to claim 1 wherein said O-ring is mounted on an inside surface of the barrel and lying in a radial plane of the axis of the barrel, and wherein there is provided an abutment surface on one side of the O-ring lying in a radial plane of the axis of the barrel and an adjustment abutment member on an opposed side of the O-ring lying in a second radial plane of the axis of the barrel, the adjustment abutment member being connected to the barrel by a screw thread coupling such that rotation of the adjustment abutment member relative to the barrel causes movement of the adjustment abutment member longitudinally of the barrel to increase and decrease compression of the O-ring.

5. The apparatus according to claim 1 wherein the barrel includes a filling opening at said needle assembly, a portion of the needle assembly being removable to allow access to an interior of the barrel for refilling the barrel between the needle assembly and the piston and for returning the piston to the retracted position.

6. The apparatus according to claim 5 wherein the needle assembly comprises an end cap member having a cylindrical surface having a screw thread thereon for engagement with a cooperating screw thread at an end of the barrel and a central insert member carrying a needle projecting axially therefrom, the central insert member having a screw thread thereon for engagement with a screw thread provided on the cap member.

7. The apparatus according to claim 1 including a pole having a receptacle receiving said barrel at an end of the barrel opposite to said needle assembly for manually supporting the barrel into engagement with the animal, and means mounted on the pole and engageable with said piston to provide said axial force on the release means.

8. The apparatus according to claim 7 wherein the release means is arranged such that actuation thereof causes said release of the piston to move forwardly while the barrel is retained in contact with said receptacle, the receptacle and the barrel being separable to allow movement of the barrel from the receptacle and wherein there is provided a string having a forward end attached to the barrel and a rearward end attached to the pole for pulling the barrel and needle assembly from the animal when the injection is complete.

9. The apparatus according to claim 8 wherein the string is stored within a hollow interior of the pole and said forward end thereof emerges from the pole at the receptacle for attachment to the barrel.

10. The apparatus according to claim 1 including means for adjusting the distance between the release member and the piston so as to vary the amount of liquid retained between the piston and the needle assembly.

11. A drug injection apparatus for remotely injecting an animal with a liquid comprising a cylindrical barrel defining a longitudinally axis of the barrel, a needle assembly at a forward end of the barrel, a piston slideable longitudinally within the barrel from a retracted position remote from the needle assembly, in which a liquid to be injected is introduced into the barrel between the needle assembly and a forward end of the piston, and a forward dispensing position in which the piston is moved forwardly to force the liquid through the needle assembly for injecting into the animal, spring means biasing the piston into the forward dispensing position, release means actuable to hold the piston in the retracted position and to release the piston to move to the forward dispensing position in response to a forward axial force on the release means, said needle assembly including a needle having a retaining member thereon for engaging flesh of the animal to hold the needle in place in the animal during said injection, a pole having a receptacle at one end thereof for receiving and retaining the barrel on the pole, the pole being manually operable to engage the needle with the animal while the barrel remains in the receptacle, means on the pole at the receptacle for causing said axial force on the release means in response to movement of the barrel toward the receptacle caused by impact of the needle assembly with the animal, the release means being arranged such that the actuation thereof causes said release of the piston to move forwardly while the barrel is retained in contact with the receptacle, the receptacle and the barrel being separable to allow movement of the barrel from the receptacle and a string having a forward end attached to the barrel and a rearward end attached to the pole for pulling the barrel and needle assembly from the animal when the injection is complete.

12. The apparatus according to claim 11 wherein the string is stored within a hollow interior of the pole and said forward end thereof emerges from the pole at the receptacle for attachment to the barrel.

13. A drug injection apparatus for remotely injecting an animal with a liquid comprising a cylindrical barrel defining a longitudinally axis of the barrel, projecting means mounted on the barrel at a rearward end thereof for projecting the barrel in a forward axial direction, a needle assembly at a forward end of the barrel, a piston slideable longitudinally within the barrel from a retracted position remote from the needle assembly, in which a liquid to be injected is introduced into the barrel between the needle assembly and a forward end of the piston, and a forward dispensing position in which the forward end of the piston is moved forwardly to force the liquid through the needle assembly for injecting into the animal, spring means biasing the piston into the forward dispensing position, release means including cooperating portions on the piston and on the barrel actuable to hold the piston in the retracted position and to release the piston to move to the forward dispensing position in response to a forward axial force on the release means, and means for adjusting a longitudinal distance between the cooperating portion of the release means on the piston and the forward end of the piston so as to vary the amount of the liquid retained in the barrel between the forward end of the piston and the needle assembly when the piston is in the retracted position.

* * * * *